US00PP28201P2

(12) United States Plant Patent
Fouillet

(10) Patent No.: US PP28,201 P2
(45) Date of Patent: Jul. 18, 2017

(54) APPLE TREE NAMED 'Y101'

(50) Latin Name: *Malus domestica*
Varietal Denomination: Y101

(71) Applicant: International Fruit Obtention (IFO) GIE, Seiches sur le Loir (FR)

(72) Inventor: Valérie Fouillet, Saint Sylvain d'Anjou (FR)

(73) Assignee: International Fruit Obtentions, Seiches sur le Loir (FR)

( * ) Notice: Subject to any disclaimer, the term of this patent is extended or adjusted under 35 U.S.C. 154(b) by 0 days.

(21) Appl. No.: 14/999,020

(22) Filed: Mar. 18, 2016

(51) Int. Cl.
*A01H 5/08* (2006.01)

(52) U.S. Cl.
USPC ..... Plt./161

(58) Field of Classification Search
USPC ..... Plt./161
See application file for complete search history.

*Primary Examiner* — Annette Para
(74) *Attorney, Agent, or Firm* — Michelle Bos Legal LLC

(57) ABSTRACT

'Y101' apple tree is a new variety selected for its distinctive pink-fleshed fruit, which is well-suited for the fresh market.

6 Drawing Sheets

Latin name: *Malus domestica.*
Variety denomination: 'Y101'.

BACKGROUND OF THE VARIETY

'Y101' is a new and distinct variety of apple tree (*Malus domestica*) obtained from a controlled cross of 'Golden Delicious' (female parent, not patented)×'SJ109' (male parent, not patented) carried out at Seiches sur le Loir, France in 2006. Seeds obtained from the cross were planted at Seiches sur le Loir, and 'Y101' was selected from the resulting seedlings for propagation and further observation. 'Y101' was first asexually propagated by grafting in 2012 at Seiches sur le Loir, and has since been observed to remain true to type over successive asexually propagated generations.

BRIEF DESCRIPTION OF THE VARIETY

'Y101' apple tree is distinguished by its fruit, which has pink flesh and is well-suited for fresh consumption. 'Y101' is distinguished from its parents as shown in Tables 1 and 2 below.

TABLE 1

Comparison of 'Y101' to 'Golden Delicious'

| Characteristic | 'Y101' | 'Golden Delicious' |
|---|---|---|
| Harvest time | 7-10 days earlier than 'Golden Delicious' | Mid to late September |
| Flesh Color | Pink | White |
| Skin Color | Red-orange | Yellow |

TABLE 2

Comparison of 'Y101' to 'SJ109'

| Characteristic | 'Y101' | 'SJ109' |
|---|---|---|
| Fruit Shape | Conical | Flat-round |
| Texture | Crunchy | Mealy, soft |

TABLE 2-continued

Comparison of 'Y101' to 'SJ109'

| Characteristic | 'Y101' | 'SJ109' |
|---|---|---|
| Storageability | Moderate (2 months) | Short (less than 1 month) |
| Taste | Balanced sugar/acid | Acidic |

BRIEF DESCRIPTION OF THE PHOTOGRAPHS

The accompanying photographs of the 'Y101' variety were taken in 2015 at Seiches sur le Loir, France.

DETAILED BOTANICAL DESCRIPTION OF THE VARIETY

Figure 1:
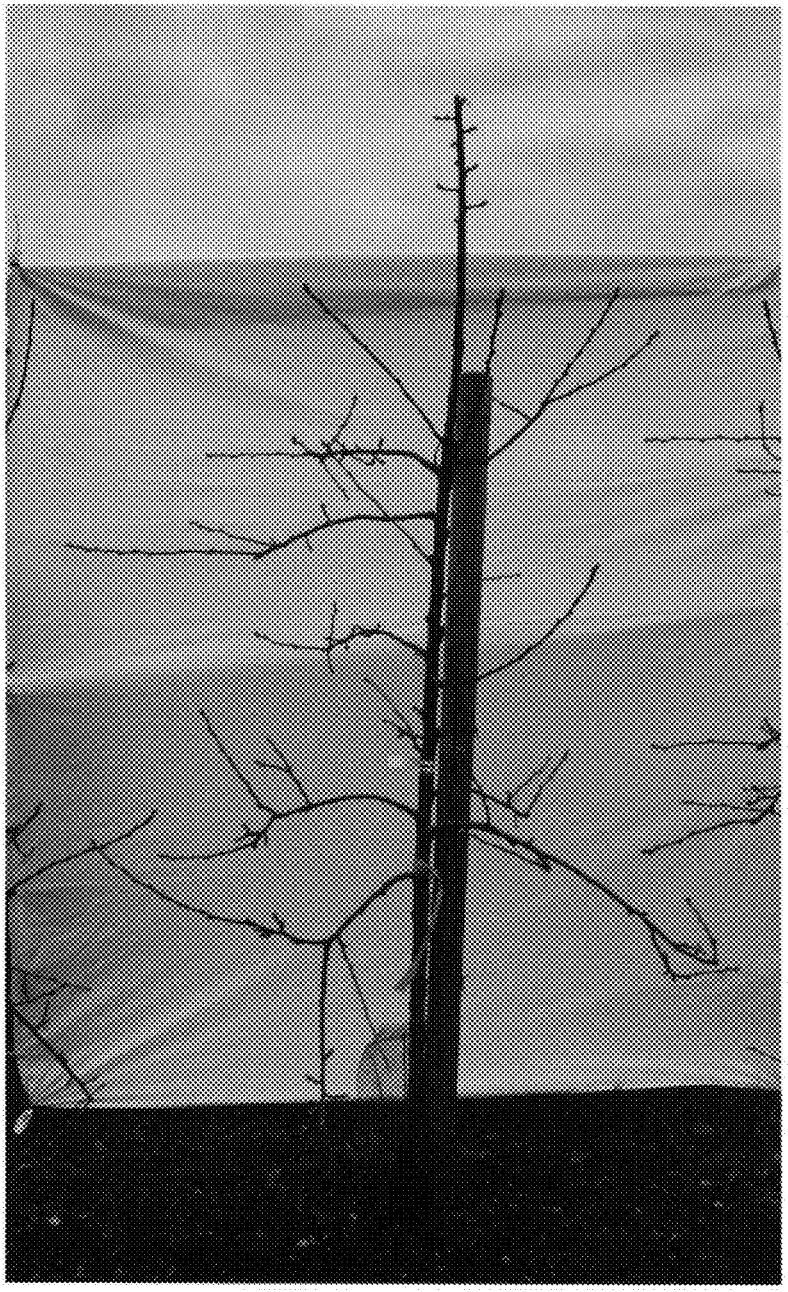
FIG. 1 is a photograph of a dormant 'Y101' apple tree.
Figure 2:
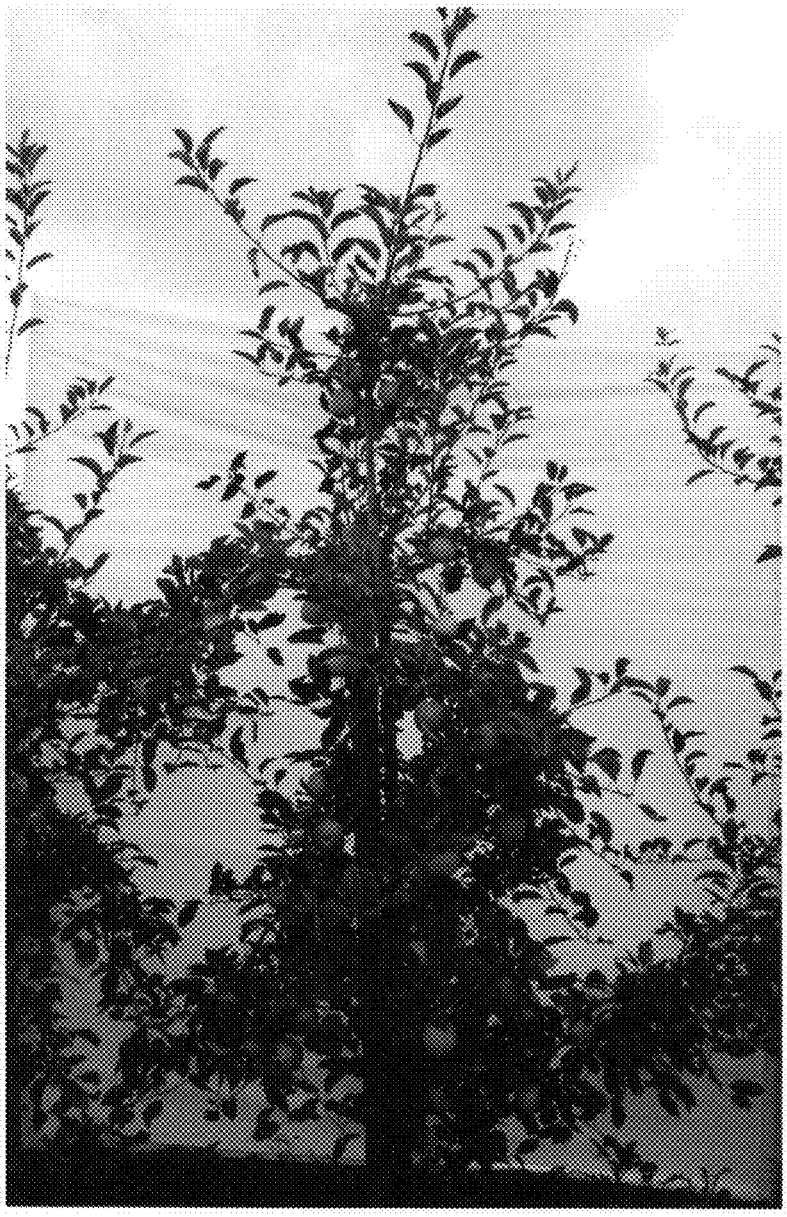
FIG. 2 is a photograph of a 'Y101' apple tree with leaves and fruit.
Figure 3:
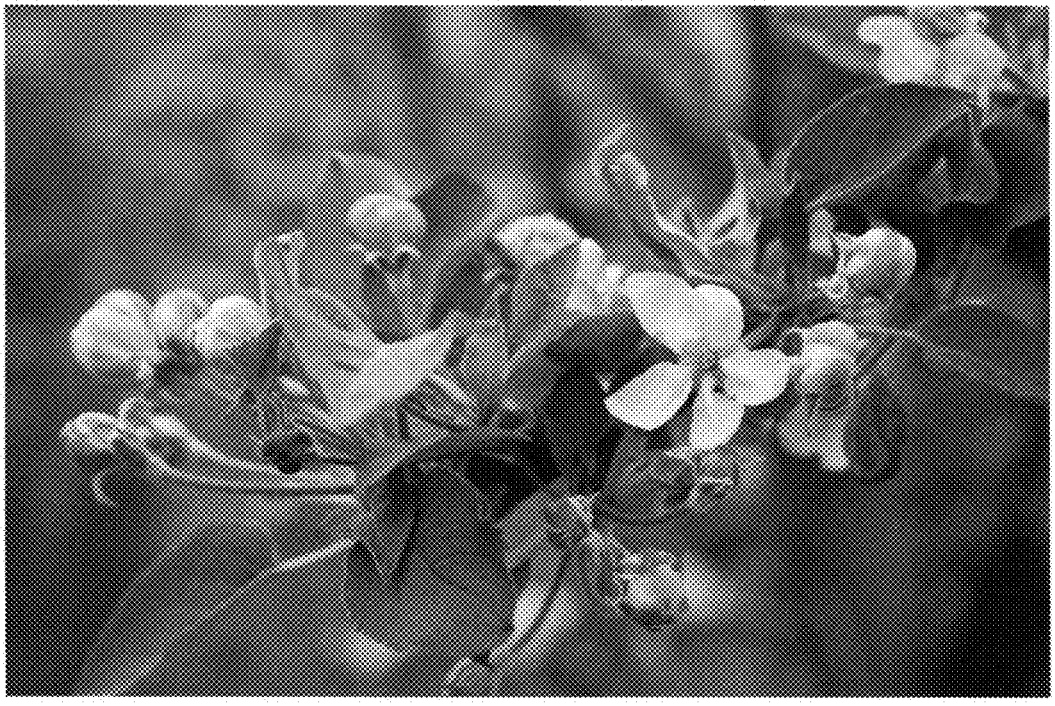
FIG. 3 is a photograph of a flower of the 'Y101' apple tree.
Figure 4:
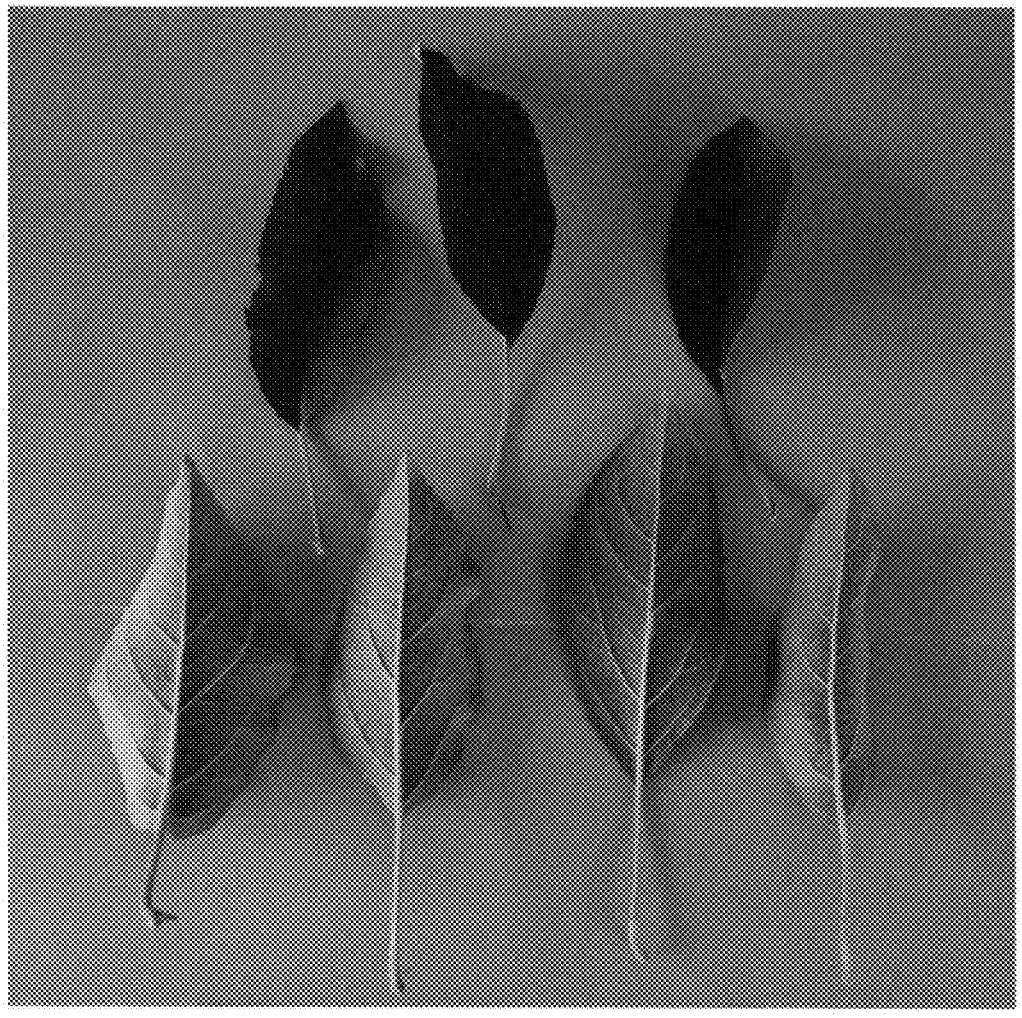
FIG. 4 is a photograph of leaves of the 'Y101' apple tree.
Figure 5:
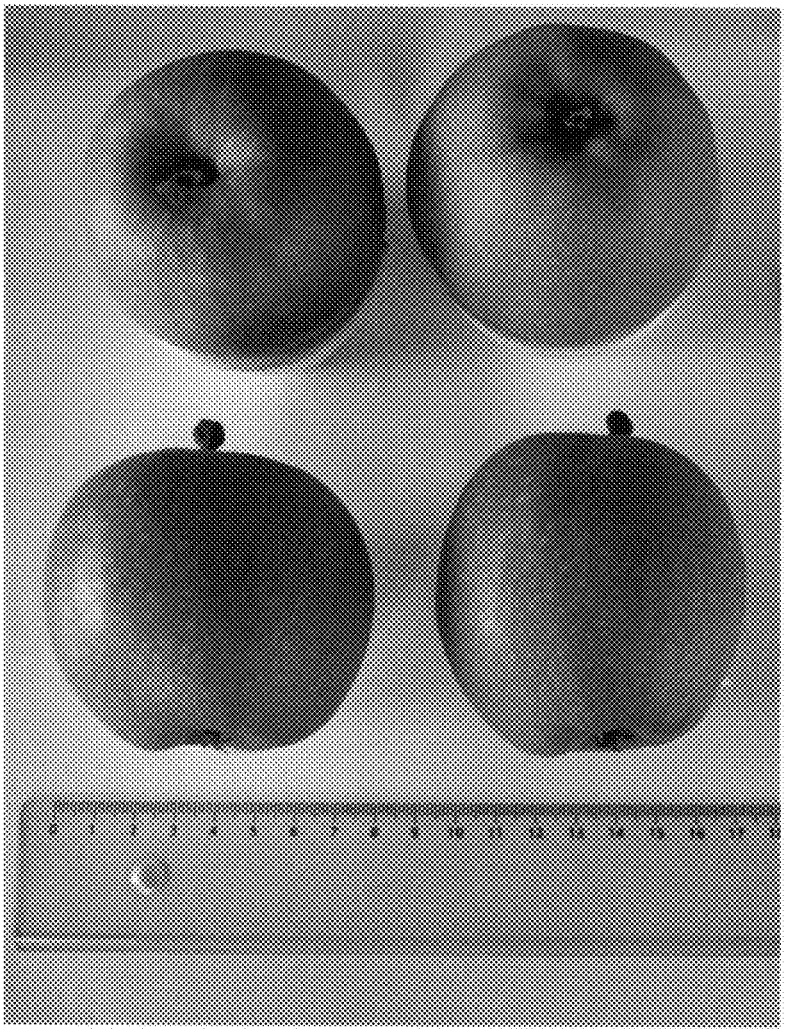
FIG. 5 is a photograph of 'Y101' apples.
Figure 6:
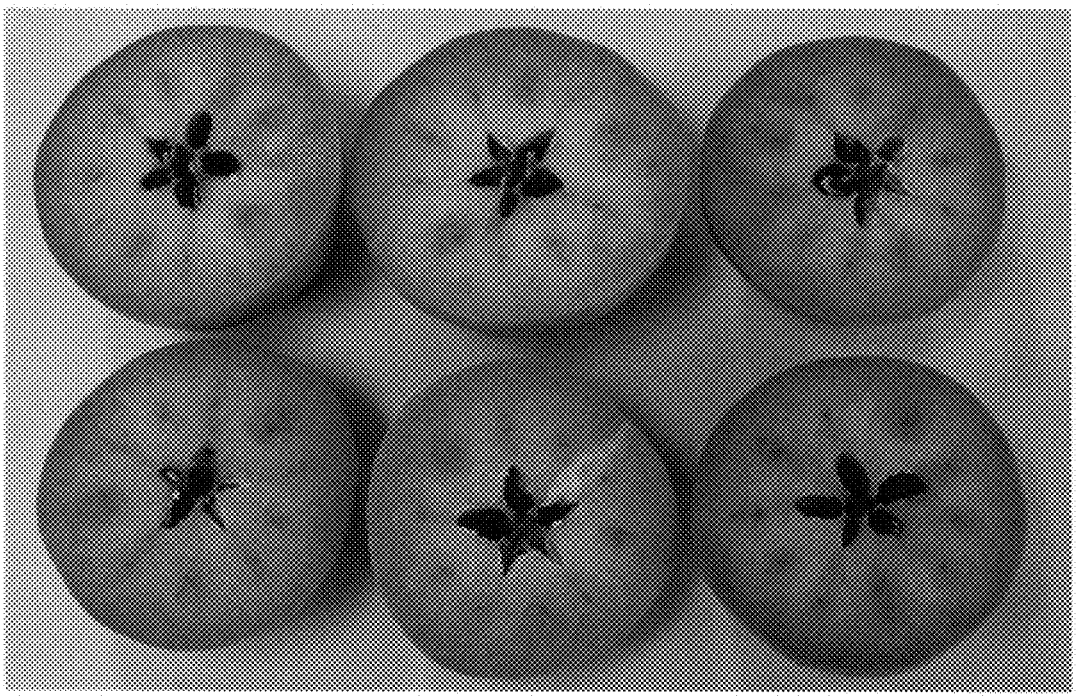
FIG. 6 is a photograph of 'Y101' apples, sectioned.

The following-detailed botanical description is based on observations made at Seiches sur le Loir, France during the 2015 growing season, of two year old trees grown on Pajam®2 'Cepiland' rootstock (U.S. Plant Pat. No. 7,715). All colors are described according to The Royal Horticultural Society Mini Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
*Vigor*.—Medium.
*Type*.—Ramified.
*Habit*.—Drooping.
*Height*.—Approximately 2.5 m.
*Trunk diameter* (*at* 30 *cm above the graft*).—31 mm.
*Bark texture*.—Smooth.
*Bark color*.—Brown 199A.

Branch (fruiting branches located at around 1 m above the graft union):
*Length*.—79 cm.
*Diameter*.—1 cm.
*Crotch angle*.—85°.
*Bark color*.—Brown 199A.
*Lenticel length*.—1 mm.
*Lenticel color*.—Light yellow 15D.
*Number of lenticels per* $cm^2$.—4.

One year old shoot:
*Length*.—29 cm.
*Color*.—Dark brown 200B.
*Pubescence*.—Absent.
*Thickness*.—5 mm.
*Internode length*.—23 mm.
*Number of lenticels per* $cm^2$.—7.

Flower buds:
*Quantity per spur*.—5.
*Shape*.—Ellipsoid.
*Length*.—12 mm.
*Diameter*.—10 mm.
*Color*.—Yellow Brown 160B.

Flowers:
*Diameter of fully open flower*.—34.6 mm.
*Relative position of petal margin*.—Intermediate.
*Number per cluster*.—5.
*Date of first bloom*.—April 14 (2015 growing season).
*Date of full bloom*.—April 18 (2015 growing season).
*Pollination requirement*.—'Gala', 'Granny Smith', and 'Golden Delicious' are suitable pollinators.

Petals:
*Number per flower*.—5.
*Shape*.—Elliptical.
*Length*.—18.4 mm.
*Width*.—13.4 mm.
*Apex*.—Obtuse.
*Base*.—Acute.
*Margin*.—Smooth.
*Color of upper surface*.—White N155B, veins light pink 56A.
*Color of lower surface*.—Purple pink 73A.

Pistils:
*Size*.—10 mm.
*Color*.—Yellow green 145B.

Stigma:
*Size*.—0.7 mm.
*Color*.—Yellow green 145A.

Style:
*Size*.—9 mm.
*Color*.—Yellow green 149D.

Ovary:
*Size*.—4.6 mm.
*Color*.—Envelope green 146C; ovules brown green 151D.

Anthers:
*Quantity*.—16.
*Size*.—2 mm.
*Presence of pollen*.—Present.
*Color of pollen*.—Light yellow 58C.

Pedicel:
*Length*.—24 mm.
*Diameter*.—1 mm.
*Color*.—Green 139C.

Sepals:
*Quantity*.—5.
*Color*.—Light green 138D.
*Shape*.—Pointed.
*Margin*.—Smooth.

Leaves:
*Shape*.—Elliptical.
*Length*.—100 mm (without stalk).
*Width*.—42 mm.
*Length/width ratio*.—2.4.
*Blade margin*.—Serrulate.
*Apex*.—Acute to acuminate.
*Base shape*.—Acute to rounded.
*Color of upper surface*.—Dark green 137A.
*Color of lower surface*.—Green 146C.
*Attitude in relation to shoot*.—Upwards.

Petiole:
*Length*.—31 mm.
*Diameter*.—1 mm.
*Color*.—Yellow green 145C with some pink violet N77B.

Fruit:
*Quantity per cluster*.—1 to 3.
*Diameter*.—71 mm.
*Weight*.—199 g.
*Height*.—65.6 mm.
*Width*.—71.1 mm.
*Height to width*.—0.92.
*General shape in profile*.—Conical.
*Position of maximum diameter*.—Equator.
*Ribbing*.—Moderate.
*Crowning at calyx end*.—Moderate.
*Size of eye*.—Medium.
*Aperture of eye*.—Closed.
*Length of sepal*.—5 mm.
*Bloom of skin*.—Moderate.
*Greasiness of skin*.—Strong.
*Amount of over color*.—90% large.
*Over color of skin*.—Orange red 34D.
*Intensity of over color*.—Medium.
*Pattern of over color*.—Solid flush.
*Amount of russet around stalk cavity*.—Medium.
*Amount of russet on cheeks*.—Absent.
*Area of russet around eye basin*.—Absent.
*Length of stalk*.—30 mm.
*Thickness of stalk*.—2 mm.
*Depth of stalk cavity*.—Medium.
*Width of stalk cavity*.—Narrow.
*Depth of eye basin*.—Shallow.
*Width of eye basin*.—Medium.
*Firmness of flesh*.—Medium.

*Flesh texture*.—Crunchy.
*Aroma*.—Balanced.
*Juiciness*.—High.
*Brix*.—13.
*Flesh color*.—80% dark pink red 52A; 20% white 155C.
*Stem color*.—Yellow green 145C.

Seeds:
*Quantity per fruit*.—7 to 10.
*Shape*.—Thick and rounded.
*Color*.—Dark brown 200D.

Harvest:
*Time for harvest*.—Early September.
*Number of picks*.—3.
*Fruit load per tree*.—Average 90 fruits.

Disease resistance/susceptibility: Resistant to scab.
Market use: Fresh consumption.

I claim:

1. A new and distinct apple tree substantially as described and illustrated herein.

* * * * *